United States Patent [19]

Aronson

[11] 4,446,868

[45] May 8, 1984

[54] CARDIAC ARRHYTHMIA ANALYSIS SYSTEM

[76] Inventor: Alfred L. Aronson, 6024 SW. Jean Rd., Lake Oswego, Oreg. 97034

[21] Appl. No.: 381,540

[22] Filed: May 24, 1982

[51] Int. Cl.³ .............................................. A61B 5/04
[52] U.S. Cl. ..................................... 128/708; 307/358
[58] Field of Search .............. 128/696, 702, 703, 704, 128/705, 706, 708, 419 D, 419 PG; 328/115, 116, 117, 120; 307/352, 358

[56] References Cited

U.S. PATENT DOCUMENTS

| | | | |
|---|---|---|---|
| Re. 30,750 | 9/1981 | Diack | 128/419 D |
| 3,707,959 | 1/1973 | Wilton-Davies | 128/703 |
| 3,841,315 | 8/1974 | Kopp | 128/706 |
| 3,878,833 | 4/1975 | Arneson | 128/708 |
| 3,927,663 | 12/1975 | Russell | 128/702 |
| 3,998,214 | 12/1976 | Garrison | 128/702 |
| 4,184,493 | 1/1980 | Langer | 128/419 D |
| 4,192,318 | 3/1980 | Dam | 128/708 |
| 4,237,903 | 12/1980 | Hofmann | 128/708 |

OTHER PUBLICATIONS

Nat'l Semiconductor Linear Application Handbook (1980) pp. AN20-8 and AN20-9.
Design of Microcomputer Based Medical Instr., Willis J. Tompkins & John G. Webster, pp. 136-139 & 412-415, 1981.
Applications of Operational Amplifiers, Gerald Graeme, pp. 111-112, 1973.

Primary Examiner—William E. Kamm
Assistant Examiner—Deidre A. Foley
Attorney, Agent, or Firm—Chernoff, Vilhauer, McClung, Birdwell & Stenzel

[57] ABSTRACT

A method and apparatus for analyzing cardiac electrical activity and producing a signal representative of the occurrence of a QRS complex. A signal representative of cardiac electrical activity is analyzed by an analog circuit that compares the sum of the rectified and low-pass filtered signal plus the derivative of the signal to a reference level, and compares the rectified and filtered signal to a threshold level, to identify QRS complexes while largely ignoring ventricular fibrillation, and produces an output pulse representative of the occurrence of a QRS complex.

6 Claims, 3 Drawing Figures

CARDIAC ARRHYTHMIA ANALYSIS SYSTEM

This invention relates to methods and apparatus for monitoring cardiac electrical activity and other life signs and triggering the application of appropriate therapeutic electrical current.

In order to save heart attack victims suffering from cardiac arrest and arrhythmias such as bradycardia (slowness of the heart beat), tachycardia (excessively rapid heart beat), and ventricular fibrillation (rapid uncoordinated fibrillary contraction of the ventricular muscle), systems have been developed for monitoring cardiac electrical activity and other life signs such as respiration, and automatically administering appropriate therapeutic electrical currents to a patient to stimulate normal cardiac activity. One such system is described in Diack et al. U.S. Pat. No. Re. 30,750 for "Cardiac Resuscitator and Monitoring Apparatus", reissued Sept. 19, 1981, and hereby incorporated by reference in its entirety.

In such systems means must be provided for accurately identifying from an electrical signal produced by the patient representative of cardiac electrical activity (hereinafter referred to for convenience as an electro-cardiac signal), in conjunction with other life signs such as the presence or absence of respiration, the existence and type of cardiac arrhythmia. Because of the complexity of the electro-cardiac signal and the variations that can occur therein depending upon the nature of the arrhythmia, accurate identification depends upon the analysis techniques utilized and the circuitry employing those techniques.

It has been found by the applicant that one previously utilized system for analyzing an electro-cardiac signal to identify the nature of an arrhythmia has not been as satisfactory as desired. That system basically employs signal conditioning by bandpass filtering, identification of waveform peaks, and comparison of the waveform amplitude to the waveform peaks to produce output pulses generally corresponding to ventricular contractions in the case of a coordinated muscular contraction or to the extremes of the oscillatory electrical activity associated with ventricular fibrillation. However, it has been found that this technique cannot discriminate between some types of cardiac arrhythmias and true ventricular fibrillation with the result that, in the presence of some unusual QRS complexes (waveforms associated with coordinated muscular contraction), the system "double counts", that is, indicates a heart beat rate twice as high as the actual ventricular contraction rate.

Other systems for identifying characteristics of an electro-cardiac signal are also known. For example, Arneson et al. U.S. Pat. No. 3,878,833 discloses a system utilizing peak detection and comparison with respect to the derivative of the electro-cardiac signal and a timing circuit for measuring the duration of an R wave candidate pulse. Another approach is illustrated by Russell et al. U.S. Pat. No. 3,927,663, where the amplitude of the rectified electro-cardiac signal is compared to a percentage thereof. A further approach is illustrated by Langer et al. U.S. Pat. No. 4,184,493 which utilizes differentiation of the electro-cardiac signal followed by threshold detection. However, it is believed that none of these provides an entirely satisfactory indication of the occurrence of a QRS complex, as distinguished from ventricular fibrillation, for use in a cardiac monitoring and resusitation system.

Accordingly, it can be seen that there is a need for improvement in cardiac monitoring and resuscitation systems, particularly in the techniques for analysis of the electro-cardiac signal for the reliable identification of a QRS complex in order to distinguish unusual as well as normal QRS events from ventricular fibrillation and to identify accurately excessively low heart rate.

Some other technical references which may be of general interest are: Garrison U.S. Pat. No. 3,998,214; Wilton-Davies U.S. Pat. No. 3,707,959; Dam et al. U.S. Pat. No. 4,192,318; Hofmann U.S. Pat. No. 4,237,903 and Kopp U.S. Pat. No. 3,841,315.

SUMMARY OF THE INVENTION

The afore-described drawbacks and limitations of prior art cardiac arrhythmia analysis systems are overcome, and additional advantages are achieved, in the present invention by the provision of a novel electro-cardiac analysis method and apparatus for implementing the same.

The system is implemented by a new circuit for detection of a QRS complex in an electro-cardiac signal. In the circuit the electro-cardiac signal is first filtered to remove dc, and very low and high frequency elements. Thereafter, the filtered electro-cardiac signal is differentiated and the derivative is summed with a scaled signal derived from the low-pass filtered absolute value of the same electro-cardiac signal. This sum is then compared to a reference level and if the sum is less than that reference level a resultant signal is produced indicating that the portion of the electro-cardiac signal being examined qualifies as a possible QRS event. Simultaneously, the filtered absolute value signal is compared to a threshold level and if the filtered absolute value signal exceeds the threshold coincident with the occurrence of the aforementioned resultant signal a pulse is produced indicative of the occurrence of a QRS event.

Accordingly, it is a principle object of the present invention to provide a new and improved cardiac arrhythmia analysis method and apparatus.

It is another object of the present invention to provide a novel method and electronic system for identifying a QRS complex in an electro-cardiac signal.

It is another object of the present invention to provide such an arrhythmia analysis method and apparatus that employs a comparison of the sum of the derivative of the electro-cardiac signal and the low-pass filtered absolute value of the electro-cardiac signal with a reference level, and a comparison of the low-pass filtered electro-cardiac signal with a threshold level to produce a reliable indication of a QRS complex.

The foregoing and other objectives, features and advantages of the present invention will be more readily understood upon consideration of the following detailed description of the invention taken in conjunction with the accompanying drawing.

DETAILED DESCRIPTION OF THE PREFERRED EMBODIMENT

The preferred embodiment of the present invention employs an electronic circuit for receiving an electrical signal representative of cardiac electrical activity, that is, an electro-cardiac signal, analyzing the signal, and producing as an output a pulse indicative of the occurrence of a QRS complex. An electro-cardiac signal with which the system will work is that which is obtained from the tongue to chest-abdominal pathway employed by the apparatus described in U.S. Pat. No. Re. 30,750, which is substantially the same as the signal obtained from a standard Lead II electrocardiogram configuration; however, the system will work with electro-cardiac signals derived from different electrocardiogram configurations, and the invention herein is not limited to a particular electro-cardiac signal.

The circuit more reliably detects the occurrence of a QRS complex and produces an output pulse in response thereto, while almost completely ignoring true ventricular fibrillation which may be identified in some other way. This is referred to herein as the "QRS circuit."

Figure 1:
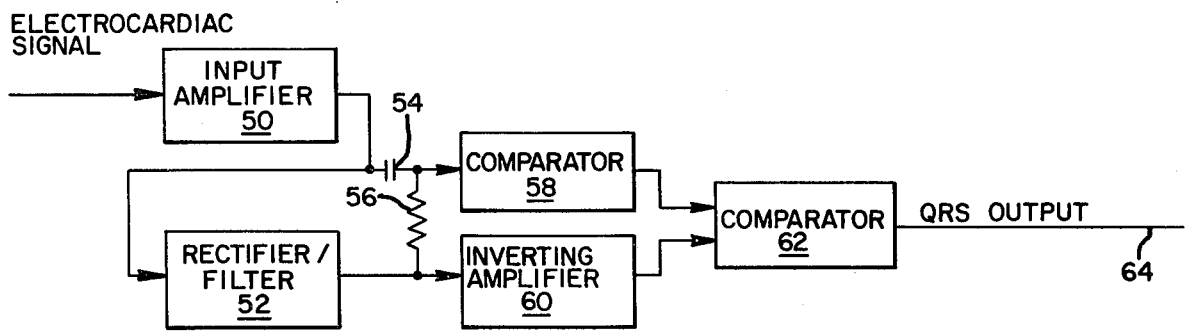
FIG. 1 is a block diagram of the preferred embodiment of the present invention.
Figure 2A:
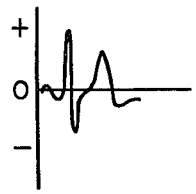
FIGS. 2A–E are exemplary signal waveforms occurring at various points of the preferred embodiment.
Figure 2B:
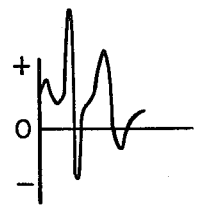

Referring to FIG. 1, the QRS circuit receives the electro-cardiac signal and amplifies and filters it by an ac input amplifier 50 having a pass-band of about 1–30 Hz. Representative waveforms of a normal electro-cardiac signal and of the output of amplifier 50 are shown in FIGS. 2A and 2B, respectively.

Figure 2C:
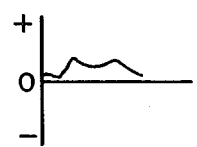

A signal representing the low-pass filtered absolute value of the filtered electro-cardiac signal, illustrated by the waveform in FIG. 2C, is produced by a full-wave rectifier and low-pass filtering circuit 52. A circuit of this type was previously known and described at pp. AN20-8 and -9 of the National Semiconductor *Linear Application Handbook* (1980). As can be seen by the waveform in FIG. 2C, a normal QRS complex causes the output of the rectifier and filtering circuit 52 to rise rather sharply and peak in the vicinity of the RS transition and thereafter decrease, typically rising again somewhat upon the occurrence of a T wave.

The filtered electro-cardiac signal is differentiated by capacitor 54, whose resultant current is summed with a scaled current through resistor 56 derived from the low-pass filtered absolute value of the same electro-cardiac signal. This current sum is presented to a comparator 58, which is referenced to signal ground. The output of this comparator is determined by the direction of input current to the comparator, that is, when the differentiated electro-cardiac signal current is negative and exceeds the amplitude of the scaled, low-pass filtered absolute value current, which is necessarily positive, then the comparator output will swing high, being limited in voltage by a zener diode feedback loop.

Figure 2D:
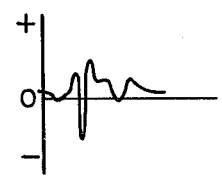
Figure 2E:
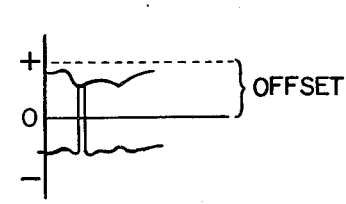

As shown by the waveform in FIG. 2D, for a normal QRS complex the negative-going R-S transition produces a distinct negative dip in the waveform representing the sum of these two signals, which triggers comparator 58, thereby producing the bottom waveform shown in FIG. 2E. In the case of a ventricular fibrillation signal, however, the relative magnitudes of the differentiated electro-cardiac signal and the rectified and filtered electro-cardiac signal are such that a negative current sum capable of triggering the comparator is only infrequently produced.

The rectified and filtered electro-cardiac signal is inverted by inverting amplifier 60, which also provides an adjustable amount of gain and offset. The output of the comparator 58 is then compared to the rectified and filtered electro-cardiac signal by comparator 62. The output of comparator 58 is input to the noninverting input of the comparator 62. The output of the inverting amplifier 60 is input to the inverting input of the comparator 62. Consequently, the output of comparator 58, essentially a pulse of predetermined amplitude, is compared to an inverted, offset rectified and filtered electro-cardiac signal, as shown by the waveforms in FIG. 2E.

It has been found that a reliable indication of the occurrence of a QRS complex is the existence of a condition where the total of the comparator 58 output signal plus the rectified and filtered electro-cardiac signal, less a predetermined offset value is greater than zero. This is illustrated by the waveforms shown in FIG. 2E wherein the lowest dip of the downwardly extending envelope of the inverted and offset average energy signal, which coincides generally with the occurrence of an R-S transition, overlaps the upwardly extending envelope of comparator 58 output, which also coincides generally with an R-S transition. This produces a pulse at the QRS output 64 from the comparator 62. Since the output of the comparator 58 is a pulse of fixed amplitude, the effect is to produce a QRS pulse when the sum of the derivative of the electro-cardiac signal plus the rectified and filtered electro-cardiac signal is negative, and the rectified and filtered electro-cardiac signal exceeds a threshold level. In the case of ventricular fibrillation the rectified and filtered electro-cardiac signal does not typically dip down in the same manner and output pulses are not usually produced by the comparator 58.

Figure 3:
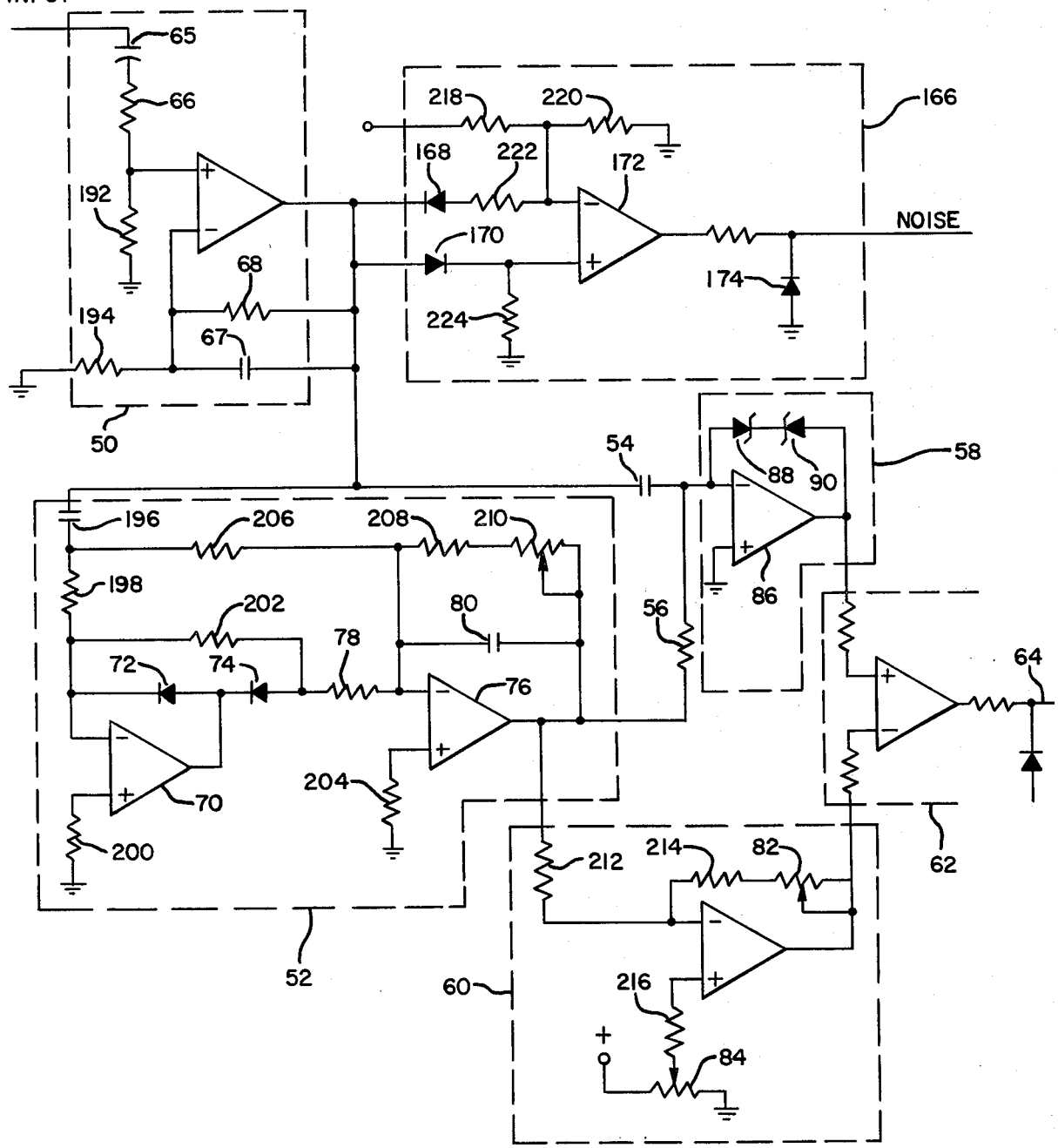
FIG. 3 is a schematic diagram of the preferred embodiment.

A schematic diagram of a QRS circuit according to the preferred embodiment is shown in FIG. 3. In the input amplifier 50, the low frequency cut off is determined primarily by capacitor 65 and resistor 66. The high frequency cutoff is determined primarily by capacitor 67 and resistor 68.

The rectifier and averaging circuit 52 employs a full-wave rectifier comprising basically amplifier 70 and diodes 72 and 74, and a low-pass filter comprising basically amplifier 76, resistor 78 and capacitor 80. The output is inverted by the inverting amplifier 60, which has in variable resistor 82 a gain control and in variable resistor 84 an output offset control.

Differentiation is accomplished by capacitor 54. The comparator 58 employs an amplifier 86 with back-to-back zener diodes 88 and 90 in a negative feedback loop. These diodes limit the positive and negative voltage excursions of the comparator output, thereby ensuring that a pulse resulting from a QRS complex will have predetermined amplitude.

Some typical values for components in a QRS circuit of the type described herein are shown in Table 1 hereof.

TABLE 1
SOME TYPICAL COMPONENT VALUES IN THE ORS CIRCUIT

| Component | Value |
|---|---|
| 54 | .01 mfd |
| 56 | 1M ohm |
| 65 | .22 mfd |
| 66 | 10K ohms |
| 67 | .01 mfd |
| 68 | 1M ohm |
| 78 | 100K ohms |
| 80 | .68 mfd |
| 82 | 10K ohms |
| 84 | 10K ohms |

TABLE 1-continued

SOME TYPICAL COMPONENT VALUES IN THE ORS CIRCUIT

| Component | Value |
|---|---|
| 192 | 1M ohm |
| 194 | 10K ohms |
| 196 | .47 mfd |
| 198 | 200K ohms |
| 200 | 100K ohms |
| 202 | 200K ohms |
| 204 | 47K ohms |
| 206 | 200K ohms |
| 208 | 100K ohms |
| 210 | 100K ohms |
| 212 | 10K ohms |
| 214 | 5.1K ohms |
| 216 | 10K ohms |
| 218 | 15K ohms |
| 220 | 56K ohms |
| 222 | 10K ohms |
| 224 | 10K ohms |

The terms and expressions which have been employed in the foregoing specification are used therein as terms of description and not of limitation, and there is no intention, in the use of such terms and expressions, of excluding equivalents of the features shown and described or portions thereof, it being recognized that the scope of invention is defined and limited only by the claims which follow.

What is claimed is:

1. A system for identifying a QRS complex in an electro-cardiac signal representative of cardiac electrical activity, comprising:
   (a) differentiator means, responsive to said electro-cardiac signal, for producing the derivative thereof;
   (b) rectifying and filtering means, responsive to said electro-cardiac signal, for producing a signal representative of the low-pass filtered absolute value of said electro-cardiac signal;
   (c) first comparator means, responsive to the derivative of said electro-cardiac signal and to said low-pass filtered absolute value signal, for producing a resultant signal when the total of a predetermined reference level less the sum of said derivative and said low-pass filtered absolute value signal is greater than zero; and
   (d) output means, responsive to said resultant signal and to said low-pass filtered absolute value signal, for producing an output signal representative of the occurrence of a QRS complex upon the occurrence of said resultant signal when the amplitude of said low-pass filtered absolute value signal exceeds a predetermined threshold level.

2. The system of claim 1 further comprising filtering means for first attenuating components of said electro-cardiac signal below about 1 Hz and above about 30 Hz a predetermined amount.

3. The system of claim 1 wherein said rectifying and filtering means comprises a full wave rectifying circuit followed by a low-pass filter.

4. The system of claim 1 wherein said first comparator means comprises a summing circuit for adding said derivative to said low-pass filtered absolute value signal and amplifier means for producing said resultant signal when the total of said predetermined reference level less the sum of said derivative and said low-pass filtered absolute value signal is greater than zero.

5. The system of claim 4, wherein said first comparator means further comprises limiter means, responsive to the output of said amplifier means, for limiting the amplitude of said resultant signal to said predetermined threshold level, and said output circuit comprises inverter means for inverting said low-pass filtered absolute value signal, said inverter means having means for providing a dc offset to the output thereof, and second comparator means for subtracting the output of said inverter means from said resultant signal and producing an output pulse when the difference is greater than zero.

6. A method for analyzing an electro-cardiac signal to detect the occurrence of a QRS complex, comprising:
   (a) differentiating the electro-cardiac signal;
   (b) rectifying and filtering the electro-cardiac signal;
   (c) adding the derivative of the electro-cardiac signal to the rectified and filtered electro-cardiac signal to produce a sum signal;
   (d) comparing said sum signal to a reference level; and
   (e) comparing said rectified and filtered electro-cardiac signal to a predetermined threshold level, the occurrence of a QRS complex being indicated by the simultaneous occurrence of the sum of the derivative of said electro-cardiac signal and the rectified and filtered electro-cardiac signal being less than said reference level and said rectified and filtered electro-cardiac signal exceeding said threshold level.

* * * * *

UNITED STATES PATENT AND TRADEMARK OFFICE
CERTIFICATE OF CORRECTION

PATENT NO. : 4,446,868
DATED : May 8, 1984
INVENTOR(S) : Bradford K. Cox

It is certified that error appears in the above-identified patent and that said Letters Patent is hereby corrected as shown below:

On the title page under "United States Patent /19/" the name "Aronson" should be deleted and -- Cox -- substituted therefor.

In item /76/ Inventor: the name "Alfred L. Aronson" should be deleted and -- Bradford K. Cox -- substituted therefor.

Signed and Sealed this

Seventeenth Day of July 1984

[SEAL]

Attest:

GERALD J. MOSSINGHOFF

Attesting Officer — Commissioner of Patents and Trademarks

UNITED STATES PATENT AND TRADEMARK OFFICE
CERTIFICATE OF CORRECTION

PATENT NO. : 4,446,868

DATED : May 8, 1984

INVENTOR(S) : Alfred L. Aronson

It is certified that error appears in the above-identified patent and that said Letters Patent is hereby corrected as shown below:

Change inventor from "Alfred L. Aronson, 6024 SW. Jean Rd., Lake Oswego, Oreg. 97034" to --Bradford K. Cox, 301 Foothills Drive, Newberg, Oreg. 97132--.

After Claim 6 insert Claim 7 as follows:

--7. In a system for identifying a QRS complex in an electro-cardiac signal representative of cardiac electrical activity, the combination comprising:

(a)    differentiator means, responsive to said electro-cardiac signal, for producing the derivative thereof;

(b)    rectifying and filtering means, responsive to said electro-cardiac signal; for producing a signal representative of the low-pass filtered absolute value of said electro-cardiac signal; and

UNITED STATES PATENT AND TRADEMARK OFFICE
CERTIFICATE OF CORRECTION

PATENT NO. : 4,446,868

DATED : May 8, 1984

INVENTOR(S) : Alfred L. Aronson

It is certified that error appears in the above-identified patent and that said Letters Patent is hereby corrected as shown below:

>    (c)   comparator means, responsive to the derivative of said electro-cardiac signal and to said low-pass filtered absolute value signal, for producing a resultant signal when the total of a predetermined reference level less the sum of said derivative and said low-pass filtered absolute value signal is greater than zero.--

On the title page after the Abstract "6 Claims, 3 Drawing Figures" should read --7 Claims, 3 Drawing Figures--.

Signed and Sealed this

*Twenty-seventh* Day of *November 1984*

[SEAL]

*Attest:*

GERALD J. MOSSINGHOFF

*Attesting Officer*     *Commissioner of Patents and Trademarks*